(12) United States Patent
Kitagawa et al.

(10) Patent No.: US 8,324,425 B2
(45) Date of Patent: Dec. 4, 2012

(54) METHOD FOR PRODUCING BICYCLIC γ-AMINO ACID DERIVATIVE

(75) Inventors: Yutaka Kitagawa, Kanagawa (JP); Makoto Imai, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/241,933

(22) Filed: Sep. 23, 2011

(65) Prior Publication Data

US 2012/0071685 A1 Mar. 22, 2012

Related U.S. Application Data

(63) Continuation of application No. PCT/JP2010/055202, filed on Mar. 25, 2010.

(30) Foreign Application Priority Data

Mar. 26, 2009 (JP) .................................. 2009-075792

(51) Int. Cl.
*C07C 227/34* (2006.01)
*C07C 229/32* (2006.01)
*A61K 31/195* (2006.01)
*A61K 31/215* (2006.01)
*A61P 25/04* (2006.01)
*A61P 43/00* (2006.01)

(52) U.S. Cl. ......... 562/401; 562/402; 560/118; 560/119

(58) Field of Classification Search ........................ None
See application file for complete search history.

(56) References Cited

U.S. PATENT DOCUMENTS

| 7,947,738 B2 | 5/2011 | Shimada et al. |
| 2003/0078300 A1 | 4/2003 | Blakemore et al. |
| 2004/0116525 A1 | 6/2004 | Derrick |
| 2010/0104575 A1 | 4/2010 | Sooknanan et al. |
| 2010/0249229 A1 | 9/2010 | Shimada et al. |

FOREIGN PATENT DOCUMENTS

| CA | 2719892 | 10/2009 |
| JP | 2006-501297 A | 1/2006 |
| WO | WO-99/21824 | 5/1999 |
| WO | WO-01/28978 | 4/2001 |
| WO | WO-02/085839 | 10/2002 |
| WO | WO-2004/006836 | 1/2004 |
| WO | WO-2009/041453 | 4/2009 |

OTHER PUBLICATIONS

Bryans, , "Identification of Novel Ligands for the Gabapentin Binding Site on the $\alpha_2\delta$ Subunit of a Calcium Channel and Their Evaluation as Anticonvulsant Agents", *J. Med. Chem.* (*41*) 1998, 1838-1845.

Frampton, James E. et al., "Pregabalin: In the Treatment of Painful Diabetic Peripheral Neuropathy", *Drugs*, vol. 64, No. 24 2004, 2813-2820.

Gee, Nicolas S. et al., "The Novel Anticonvulsant Drug, Gabapentin (Neurontin), Binds to the $\alpha_2\delta$ Subunit of a Calcium Channel", *Journal of Biological Chemistry*, vol. 271, No. 10 Mar. 8, 1996, 5768-5776.

Mann, Andre et al., "Synthesis and Biochemical Evaluation of Baclofen Analogs Locked in the Baclofen Solid-State Conformation", *Journal of Medicinal Chemistry*, vol. 34, No. 4 1991, 1307-1313.

Nicholson, B. , "Gabapentin use in neuropathic pain syndromes", *Acta Neurol Scand*, vol. 101 2000, 359-371.

Cott, Jerry, "Pharmacology Reviews," *Pharmacology/Toxicology Review and Evaluation*, Food and Drug Administration, Center for Drug Evaluation and Research, NDA No. 21-446, May 24, 2004, pp. 1-136.

Avenoza, Alberto et al. "Synthesis of enantiopure analogues of 3-hydroxyproline and derivatives," *Tetrahedron: Asymmetry*, vol. 13, pp. 625-632 (2002).

*Primary Examiner* — Yevegeny Valenrod
(74) *Attorney, Agent, or Firm* — Dorsey & Whitney LLP

(57) ABSTRACT

Methods for producing compounds having activity as an $\alpha_2\delta$ ligand are provided.

6 Claims, No Drawings

METHOD FOR PRODUCING BICYCLIC γ-AMINO ACID DERIVATIVE

This application is a Continuation of PCT Patent Application No. PCT/JP2010/055202, filed Mar. 25, 2010, entitled "METHOD FOR PRODUCING BICYCLIC γ-AMINO ACID DERIVATIVE," which claims priority to Japanese Application No. 2009-075792, filed Mar. 26, 2009, the contents of all of which are hereby incorporated in their entirety by reference.

TECHNICAL FIELD

The present invention relates to a bicyclic γ-amino acid derivative or a pharmacologically acceptable salt thereof. Particularly, the present invention relates to a compound having activity as an $\alpha_2\delta$ ligand and affinity for voltage-dependent calcium channel subunit $\alpha_2\delta$, or a method for producing the same.

BACKGROUND ART

Compounds that exhibit high-affinity binding to voltage-dependent calcium channel subunit $\alpha_2\delta$ have been shown to be effective for treating, for example, neuropathic pain (see e.g., Non Patent Literatures 1 and 2). In this context, neuropathic pain refers to chronic pain caused by nervous tissue injury or the like and is a disease that significantly impairs the quality of life in such a way that patients suffer from depression due to severe pain attacks.

Several types of $\alpha_2\delta$ ligands are currently known as therapeutic drugs for such neuropathic pain. Examples of $\alpha_2\delta$ ligands include gabapentine and pregabalin. $\alpha_2\delta$ ligands such as these compounds are useful for treating epilepsy and neuropathic pain or the like (e.g., Patent Literature 1).

However, it has been reported that, for example, for gabapentine, its efficacy in the treatment of postherpetic neuralgia is approximately 60% according to patients' own evaluation (see e.g., Non Patent Literature 3) and that for pregabalin, its efficacy in the treatment of painful diabetic neuropathy is approximately 50% according to patients' own evaluation (see e.g., Non Patent Literature 4).

Other compounds are disclosed in, for example, Patent Literatures 2, 3, and 4.

CITATION LIST

Patent Literature

Patent Literature 1: International Publication No. WO 04/006836
Patent Literature 2: International Publication No. WO 99/21824
Patent Literature 3: International Publication No. WO 01/28978
Patent Literature 4: International Publication No. WO 02/085839

Non-Patent Literature

Non-patent Literature 1: J Biol. Chem. 271 (10): 5768-5776, 1996
Non-patent Literature 2: J Med. Chem. 41: 1838-1845, 1998
Non-patent Literature 3: Acta Neurol. Scand. 101:359-371, 2000
Non-patent Literature 4: Drugs 64 (24): 2813-2820, 2004

SUMMARY OF INVENTION

Technical Problem

An object of the present invention is to provide a method for producing a bicyclic γ-amino acid derivative having excellent activity as an $\alpha_2\delta$ ligand and an intermediate for producing the same, and salts thereof.

Solution to Problem

The present invention will be described below.

(1) A method for producing a compound represented by the general formula (I) or a salt thereof by optical resolution:

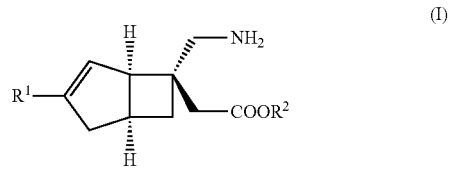

wherein each substituent is defined as follows:

$R^1$: a hydrogen atom or a C1-C6 alkyl group, and
$R^2$: a hydrogen atom or a protective group for the carboxy group, the method comprising dissolving a mixture of compounds represented by the general formulas (II), (III), (IV), and (V) and an optically active organic acid in a solvent:

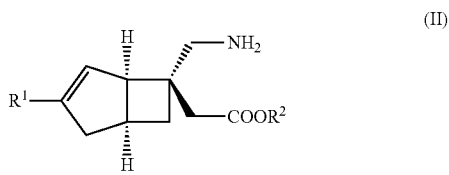

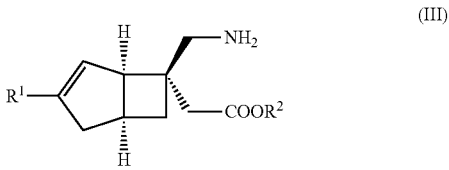

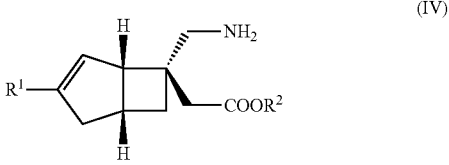

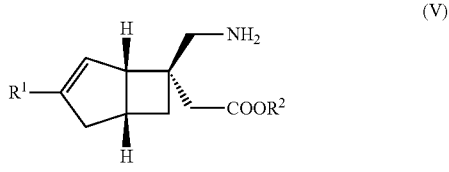

and then depositing a crystal.

Moreover, aspects of the present invention are preferably as shown below.

(2) The method for producing a compound represented by the general formula (I) or a salt thereof according to (1), wherein $R^1$ is a hydrogen atom, a methyl group, or an ethyl group.

(3) The method for producing a compound represented by the general formula (I) or a salt thereof according to (1) or (2), wherein $R^2$ is a t-butyl group.

(4) The method for producing a compound represented by the general formula (I) or a salt thereof according to any one of (1) to (3), wherein the optically active organic acid is any active organic acid selected from the following group:

D-mandelic acid, L-mandelic acid, Di-p-toluoyl-L-tartaric acid, N-Boc-L-proline, (R)-α-methoxyphenylacetic acid, O-acetyl-L-mandelic acid, Di-benzoyl-L-tartaric acid, O-acetyl-D-mandelic acid, N-Boc-L-alanine, (S)-2-(6-methoxy-2-naphthyl)propionic acid, diacetyl-L-tartaric acid, L-tartaric acid, L-malic acid, L-pyroglutamic acid, (+)-camphoric acid, (S)-2-methylglutamic acid, (+)-3-bromocamphor-8-sulfonic acid, (−)-menthoxyacetic acid, and (S)-2-phenoxypropionic acid.

(5) The method for producing a compound represented by the general formula (I) or a salt thereof according to any one of (1) to (4), wherein the solvent is any solvent selected from the following group:

acetonitrile, ethyl acetate, toluene, and cyclopentyl methyl ether.

Furthermore, the present invention also encompasses a production method shown below.

(6) A method for producing a compound represented by the general formula (X) or a salt thereof:

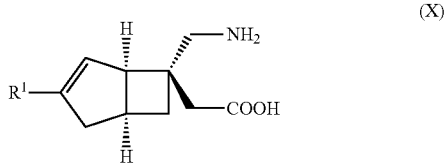

wherein each substituent is defined as follows:
$R^1$: a hydrogen atom or a C1-C6 alkyl group,
the method comprising
deprotecting a protective group for the carboxy group in a compound represented by the general formula (I) produced by a production method according to (1) or performing this deprotection and further forming an acid or a salt.

Advantageous Effects of Invention

The production method according to the present invention can provide a bicyclic γ-amino acid derivative having excellent activity as an $α_2δ$ ligand, an intermediate for producing the same, or the salts thereof.

DESCRIPTION OF EMBODIMENTS

A "C1-C6 alkyl group" refers to a linear or branched alkyl group having 1 to 6 carbon atoms and includes methyl, ethyl, propyl, isopropyl, butyl, isobutyl, sec-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl groups.

Since a compound represented by the general formula (I), or the like, having amino and/or carboxyl groups in the structure, forms a salt through reaction with an acid or a base, a "salt" or a "pharmacologically acceptable salt" refers to this salt.

In the nomenclature of compounds in the present specification, "*" represents that each compound having asymmetric carbon atoms thus indicated is a racemic mixture. However, the indication "(1S*,5R*,6R*)-" shall represent their relation in terms of relative configuration.

The compound represented by the general formula (I), or the like, when left in the air or recrystallized, may associate with adsorbed water through water absorption to form a hydrate. Such a hydrate is also encompassed by the salt of the present invention.

Examples of a "protective group for the carboxy group" include methyl, ethyl, propyl, isopropyl, butyl, isobutyl, sec-butyl, t-butyl, hexyl, bromo-tert-butyl, trichloroethyl, benzyl, p-nitrobenzyl, o-nitrobenzyl, p-methoxybenzyl, p-t-butylbenzyl, acetoxymethyl, propionyloxymethyl, butyryloxymethyl, isobutyryloxymethyl, valeryloxymethyl, pivaloyloxymethyl, acetoxyethyl, acetoxypropyl, acetoxybutyl, propionyloxyethyl, propionyloxypropyl, butyryloxyethyl, isobutyryloxyethyl, pivaloyloxyethyl, hexanoyloxyethyl, isobutyryloxymethyl, ethylbutyryloxymethyl, dimethylbutyryloxymethyl, pentanoyloxyethyl, methoxycarbonyloxymethyl, ethoxycarbonyloxymethyl, propoxycarbonyloxymethyl, t-butoxycarbonyloxymethyl, methoxycarbonyloxyethyl, ethoxycarbonyloxyethyl, isopropoxycarbonyloxyethyl, t-butyldimethylsilyl, trimethylsilyl, methoxymethyl, ethoxymethyl, propoxymethyl, isopropoxymethyl, (2-methylthio)-ethyl, 3-methyl-2-butenyl, 5-indanyl, and 3-phthalidyl groups. The protective group is preferably a t-butyl group.

The carboxyl group in the compound represented by the general formula (I) can be deprotected by a usual method for deprotecting carboxy groups, for example, a method described in T. W. Greene and P. G. Wuts, "Protective Groups in Organic Synthesis (3rd ed., 1999)" to produce a compound represented by the general formula (X).

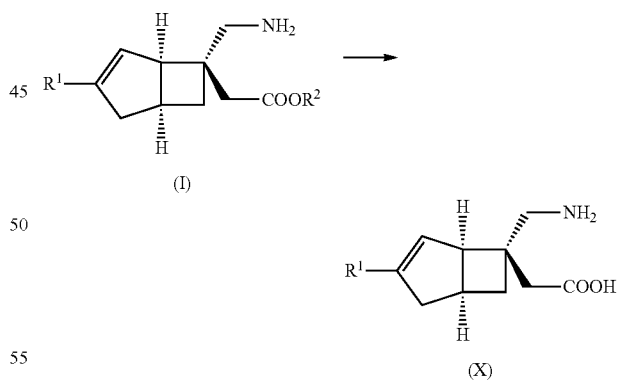

The compound represented by the general formula (X) or a pharmaceutically acceptable salt thereof exhibits activity as an $α_2δ$ ligand and affinity for voltage-dependent calcium channel subunit $α_2δ$ and is useful as an active ingredient in a pharmaceutical composition used for treating and/or preventing pain, central nervous system involvement, and other disorders.

A pharmaceutical composition comprising the compound having the general formula (X) or the pharmacologically acceptable salt thereof, when administered to mammals (e.g., humans, horses, cow, or pigs, preferably humans), is administered systemically or locally through an oral or parenteral route.

The pharmaceutical composition of the present invention can be prepared in an appropriate form selected according to the administration method, by preparation methods usually used for various preparations.

Forms of the pharmaceutical composition for oral administration include tablets, pills, powders, granules, capsules, solutions, suspensions, emulsions, syrups, and elixirs. The pharmaceutical composition in such a form is prepared according to a standard method by appropriately selecting, according to need, additives from among excipients, binders, disintegrants, lubricants, swelling agents, swelling aids, coating agents, plasticizers, stabilizers, antiseptics, antioxidants, coloring agents, solubilizers, suspending agents, emulsifiers, sweeteners, preservatives, buffers, diluents, wetting agents, etc. usually used.

Forms of the pharmaceutical composition for parenteral administration include injections, ointments, gels, creams, poultices, patches, aerosols, inhalants, sprays, eye drops, nasal drops, and suppositories. The pharmaceutical composition in such a form is prepared according to a standard method by appropriately selecting, according to need, additives from among stabilizers, antiseptics, solubilizers, humectants, preservatives, antioxidants, flavors, gelling agents, neutralizing agents, solubilizers, buffers, tonicity agents, surfactants, coloring agents, buffering agents, thickeners, wetting agents, fillers, absorption promoters, suspending agents, binders, etc. usually used.

The dose of the compound having the general formula (X) or the pharmacologically acceptable salt thereof differs depending on symptoms, age, body weight, etc., and is, for oral administration, 1 to 2000 mg, preferably 10 to 600 mg (in terms of the amount of the compound) per dose to a human adult (body weight: approximately 60 Kg) and, for parenteral administration, 0.1 to 1000 mg, preferably 1 to 300 mg (in terms of the amount of the compound) per dose to an adult.

EXAMPLES

Preparation Example 5 g of the compound having the general formula (X), 90 g of lactose, 34 g of corn starch, 20 g of crystalline cellulose, and 1 g of magnesium stearate are mixed using a blender and then compressed using a tableting machine to obtain a tablet.

Test Example 1

Construction of Human Calcium Channel Subunit $\alpha_2\delta_1$ (Hereinafter, Referred to Human Cacna2d1) Gene Expression Plasmid, and Preparation of Human Cacna2d1-Expressing Cell Membrane Fraction Construction of human Cacna2d1 expression plasmid pRK/hCacna2d1 a-1) Preparation of DNA Fragment

The human Cacna2d1 gene was obtained as two fragments, the first half and second half fragments. PCR was performed using a cDNA library (QUICK-Clone cDNA Human Brain (Clontech Laboratories, Inc.)) as a template and an enzyme KOD polymerase (TOYOBO CO., LTD.) according to the protocol included with this enzyme. PCR primers used were, for the first half fragment, primers having the following sequences:

Primer 1: 5'-agctgcggcc gctagcgcca ccatggctgg ctgcctgctg gc-3' (SEQ ID NO: 1), and Primer 2: 5'-attaggatcg attgcaaagt aataccc-3' (SEQ ID NO: 2); and for the second half fragment, primers having the following sequences:

Primer 3: 5'-aatgggtatt actttgcaat cgatcc-3' (SEQ ID NO: 3), and

Primer 4: 5'-agtcggatcc tcataacagc cggtgtgtgc tg-3' (SEQ ID NO: 4)

purchased from SIGMA GENOSYS. The PCR reaction was performed for both the first half and second half fragments using a thermal cycler (GeneAmp PCR System 9700 (Applied Biosystems, Inc.)) through a process involving heating at 94° C. for 1 minute, then 35 thermal cycles (94° C. for 15 sec., 60° C. for 30 sec., and 68° C. for 2 min.), placing at 68° C. for 5 minutes, and cooling to 4° C.

These two reaction products were purified using a PCR product purification kit (MiniElute PCR Purification Kit (QIAGEN)) according to the protocol included in this kit. The obtained first half fragment was digested with a restriction enzyme Not1 (TOYOBO CO., LTD.). The second half fragment was digested with restriction enzymes Cla1 (TOYOBO CO., LTD.) and BamH1 (TOYOBO CO., LTD.). Subsequently, these fragments were purified using a reaction product purification kit (MiniElute Reaction Cleanup Kit (QIAGEN)) according to the protocol included in this kit.

a-2) Preparation of Vector

The multicloning site (hereinafter, referred to as MCS) of an expression vector pRK5 for animal cells (BD Pharmingen) was changed to the MCS of a vector pBluescript 2 (STRATAGENE) to prepare a vector. Specifically, pRK5 was treated with restriction enzymes Cla1 (TOYOBO CO., LTD.) and Hind3 (TOYOBO CO., LTD.), and both the ends of this DNA were then blunt-ended using Klenow Fragment (TAKARA BIO INC.). Both of these ends were further dephosphorylated using calf intestine alkaline phosphatase (hereinafter, referred to as CIAP; TAKARA BIO INC.), and the fragment was then purified using MiniElute Reaction Cleanup Kit (QIAGEN). Then, this enzyme-treated DNA was electrophoresed on 1.0% agarose gel. After the electrophoresis, the gel was stained with ethidium bromide. Then, a band portion corresponding to approximately 4.7 kbp was separated under UV irradiation using a razor blade. DNA was extracted therefrom using a gel extraction/purification kit (MiniElute Gel Extraction Kit (QIAGEN)) according to the protocol included in this kit.

To obtain a DNA fragment corresponding to the MCS of pBluescript 2, pBluescript 2 was treated with restriction enzymes Sac1 (TOYOBO CO., LTD.) and Kpn1 (TOYOBO CO., LTD.), and both the ends of this DNA were then blunt-ended using Klenow Fragment (TAKARA BIO INC.). Then, this enzyme-treated DNA was electrophoresed on 2.0% agarose gel. After the electrophoresis, the gel was stained with ethidium bromide. Then, a band portion corresponding to approximately 100 bp was separated under UV irradiation using a razor blade. DNA was extracted therefrom using a gel extraction/purification kit (MiniElute Gel Extraction Kit (QIAGEN)) according to the protocol included in this kit.

The obtained DNA fragment and the already-cleaved pRK5 were ligated using a DNA ligation kit (TAKARA BIO INC.) according to the protocol included in the kit. With this reaction product, E. coli DH5α competent cells (TOYOBO CO., LTD.) were transformed to obtain ampicillin-resistant colonies. Some of the colonies were collected, and the collected colonies were then cultured. From the obtained bacterial cells, a plasmid was extracted and analyzed for its nucleotide sequence using a DNA sequencer (Model 3700 (Applied Biosystems, Inc.)) to confirm the introduction of the MCS sequence in the pRK5. In this context, a vector in which, when the CMV promoter is viewed as being located upstream, the MCS sequence was incorporated such that it was oriented in a downstream direction as follows: 5'-ccac-cgcggtggcggccgctctagaactagtg-gatcccccgggctgcaggaattcgatatcaagcttatcgataccgtcgacctcgag gggggccccg-3' (SEQ ID NO: 5) was designated as pRK-SK, and a vector in which the MCS sequence was incorporated in an orientation opposite thereto was designated as pRK-KS.

a-3) Construction of Plasmid

The pRK-SK obtained in paragraph a-2) was treated with a restriction enzyme Xba1 (TOYOBO CO., LTD.), and both the ends of the DNA were blunt-ended using Klenow Fragment (TAKARA BIO INC.). The blunt-ended DNA was further digested with a restriction enzyme Not1 (TOYOBO CO., LTD.) and purified in the same way as in paragraph a-2). This pRK-SK thus made linear and the first half DNA fragment of the human Cacna2d1 gene obtained in paragraph a-1) were electrophoresed on 1.0% agarose gel, and DNAs of approximately 4.7 kbp and approximately 1.5 kbp were extracted from the gel and purified in the same way as in paragraph a-2). The obtained two DNAs were ligated in the same way as in paragraph a-2), and E. coli was transformed with the ligation product. From the obtained E. coli clones, a plasmid was extracted and analyzed for its nucleotide sequence using a DNA sequencer (Model 3700 (Applied Biosystems, Inc.)) to confirm the introduction of the sequence represented by SEQ ID NO: 6 therein. Next, the obtained plasmid was treated with restriction enzymes Cla1 (TOYOBO CO., LTD.) and BamH1 (TOYOBO CO., LTD.), and CIAP treatment and purification were performed in the same way as in paragraph a-2). This plasmid DNA thus made linear and the second half DNA fragment of the human Cacna2d1 gene obtained in paragraph a-1) were electrophoresed on 1.0% agarose gel, and DNAs of approximately 6.2 kbp and approximately 1.8 kbp were extracted from the gel and purified in the same way as in paragraph a-2). The obtained two DNAs were ligated in the same way as in paragraph a-2), and E. coli was transformed with the ligation product. From the obtained E. coli clones, a plasmid was extracted and analyzed for its nucleotide sequence using a DNA sequencer (Model 3700 (Applied Biosystems, Inc.)) to confirm the introduction of the sequence represented by SEQ ID NO: 7 in the vector pRK-SK. The obtained plasmid was designated as pRK/hCacna2d1.

b) Obtainment of Human Cacna2d1-Expressing 293 Cell Line 293 cells were transfected with the human Cacna2d1 expression plasmid pRK/hCacna2d1 constructed in paragraph a), and a cell line stably expressing human Cacna2d1 was obtained with human Cacna2d1 protein expression as an index. Specifically, $2\times10^6$ 293 cells were inoculated onto a φ6 cm dish and cultured for 12 hours. Then, the cells were cotransfected with 5 µg of pRK/hCacna2d1 and 0.5 µg of a neomycin-resistant gene expression plasmid pSV2neo (Clontech) using a transfection reagent Lipofectamine Plus (Invitrogen Corp.) according to the protocol included with the reagent.

The cells thus transfected were collected, then inoculated onto a φ15 cm dish after dilution, and cultured for 2 weeks in DMEM (Invitrogen Corp.) supplemented with 10% fetal bovine serum (Cansera International, Inc.) and 500 µg/ml G418 (Invitrogen Corp.). The neomycin-resistant cells that successfully formed colonies were isolated. After expansion culture, the cells were collected, and the cell lysate was evaluated by Western assay to obtain a human Cacna2d1-expressing 293 cell line. In the Western assay, anti-hCacna2d1 antibodies (Chemicon Inc.) were used as primary antibodies.

c) Preparation of Cell Membrane Fraction of Human Cacna2d1-Expressing 293 Cell

The human Cacna2d1-expressing 293 cells obtained in paragraph b) were cultured in large scale in DMEM (Invitrogen Corp.) supplemented with 10% fetal bovine serum (Cansera International, Inc.) and 500 µg/ml G418 (Invitrogen Corp.), and the cells were collected. A protease inhibitor (Complete EDTA free (Roche Applied Science)) was added in an amount recommended by the reagent to a binding assay buffer (10 mM MOPS (pH 7.4), 10 mM HEPES (pH 7.4), 100 mM NaCl) to prepare a membrane fraction preparation buffer. The collected cells were washed with the membrane fraction preparation buffer and then homogenized using an ultrasonicator. Then, the homogenate was centrifuged at 12,000 rpm at 4° C. for 1 hour using a centrifuge. The supernatant was discarded, and the precipitate was suspended in the membrane fraction preparation buffer. The procedure from the ultrasonication using a ultrasonicator to the suspension of the precipitate after centrifugation was further repeated three times, and the obtained suspension was used as a human Cacna2d1-expressing cell membrane fraction. The total level of proteins contained in the membrane fraction was calculated from UV absorbance at a wavelength of 280 nm.

Test Example 2

Construction of Detection System for Binding Reaction Between Cacna2d1 and Gabapentin (Hereinafter, Referred to as GBP), and Detection of Cacna2d1/GBP Binding Reaction Inhibitory Activities of Test Compounds a) Construction of Detection System for Binding Reaction Between Cacna2d1 and GBP The human Cacna2d1-expressing cell membrane fraction and GBP labeled with a radioisotope $^3$H (hereinafter, referred to as $^3$H-GBP; Tocris Cookson Ltd.) were diluted with a binding assay buffer (10 mM MOPS (pH 7.4), 10 mM HEPES (pH 7.4), 100 mM NaCl) at a final concentration of 2.5 mg/ml in terms of the total protein level and a final $^3$H-GBP concentration of 4.5 nM, respectively, to prepare 120 d of a reaction solution, which was in turn left standing at 4° C. for 3 hours. This reaction product was added to wells of a filter plate (UniFilter 350 GF/B (Whatman)) and filtered through the filter. Then, a washing procedure involving the addition of 350 µl of a binding assay buffer (10 mM MOPS (pH 7.4), 10 mM HEPES (pH 7.4), 100 mM NaCl) and filtration through the filter was repeated three times. The filter plate was thoroughly dried, and the underside was sealed. After addition of 50 µl of Microscint 20 (PerkinElmer Inc.), the upper surface was also sealed, and radiation derived from the radioisotope $^3$H remaining on the filter was counted using TopCount (PerkinElmer Inc.). From the obtained value, a value obtained by adding unlabeled GBP (SIGMA-ALDRICH INC.) at a final concentration of 20 µM to the present assay was subtracted as that derived from nonspecific adsorption, and the obtained value was used as the specific binding level of $^3$H-GBP to Cacna2d1 (unit: "count").

b) Detection of Cacna2d1/GBP Binding Reaction Inhibitory Activities of Test Compounds Each test compound was added at various concentrations to the Cacna2d1/GBP binding reaction detection assay constructed in paragraph a), and the binding level was measured by the method described in paragraph a). Then, with the Cacna2d1/GBP specific binding level obtained by the addition of the compound at a concentration of x nM being defined as "binding level [x]" and the Cacna2d1/GBP binding inhibitory rate thereagainst being defined as "inhibitory rate [x]", the inhibitory rate (%) was determined based on the following equation:

Inhibitory rate [x](%)=(1−(binding level [x]/binding level [0]))×100, wherein the binding level [0] refers to the binding level of $^3$H-GBP obtained without the addition of the compound.

The inhibitory rate was plotted against concentration. From this result, an "$IC_{50}$ value" was calculated, which is the concentration of the test compound necessary for inhibiting 50% of Cacna2d1/GBP binding.

Production Example 1

[6-(Aminomethyl)bicyclo[3.2.0]hept-3-en-6-yl]acetic acid

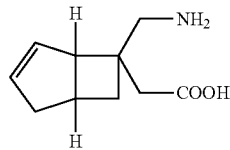

(1-a) (2E)-Hepta-2,6-dienoic acid

4-Pentenal (4.45 g, 51.4 mmol) and malonic acid (6.41 g, 61.6 mmol) were dissolved in pyridine (9.9 mL). To the solution, piperidine (1.9 mL) was added, and the mixture was then stirred at 90° C. for 5 hours. The mixture was allowed to cool and then made acidic by the addition of 2 N hydrochloric acid, followed by extraction with diethyl ether. The organic layer was washed with saturated saline and dried over anhydrous magnesium sulfate, and the filtrate was then concentrated under reduced pressure. The residue was distilled under reduced pressure to obtain the compound of interest as a colorless oil substance (3 mmHg, 110-116° C., 3.27 g, 50%).

$^1$H-NMR (400 MHz, CDCl$_3$): δ ppm: 2.21-2.26 (2H, m), 2.32-2.37 (2H, m), 5.01-5.08 (2H, m), 5.75-6.87 (2H, m), 7.03-7.11 (1H, m).

(1-b) Tert-butyl bicyclo[3.2.0]hept-3-en-6-ylideneacetate

Oxalyl chloride (10 mL) was added dropwise to a solution of (2E)-hepta-2,6-dienoic acid (3.27 g, 25.9 mmol) in toluene (60 mL) under ice cooling. The mixture was stirred for 20 minutes, then removed from the ice water bath, and gradually heated to room temperature. After stirring for 50 minutes, the reaction solution was stirred for 1 hour under heating to reflux. The solution was allowed to cool, and the solvent was then distilled off under reduced pressure. To the residue, toluene was further added, and the solvent was then distilled off again under reduced pressure. The residue was dissolved in toluene (20 mL), and this solution was added dropwise over 1 hour to a solution of triethylamine (9.19 g, 91 mmol) in toluene (20 mL) heated in advance to 90° C. After the completion of the dropwise addition, the mixture was further heated with stirring for 2 hours. The reaction solution was cooled, then diluted with saturated saline and water, and filtered through Celite. The filtrate was separated into organic and aqueous layers. The organic layer was then washed with 1 N hydrochloric acid, then dried over magnesium sulfate, and filtered. The filtrate was added to a reaction solution prepared in advance from a solution of tert-butyl dimethoxyphosphorylacetate (5.98 g, 25.9 mmol) in dimethoxyethane (20 mL) and sodium hydride (>65% oil, 986.7 mg, 25.9 mmol), and the mixture was stirred for 1.5 hours. To the reaction solution, a saturated aqueous solution of ammonium chloride, saturated saline, and water were added in this order, and the reaction solution was subjected to extraction with ethyl acetate. The organic layer was dried over anhydrous magnesium sulfate and then filtered. The solvent was distilled off under reduced pressure, and the residue was purified by silica gel column chromatography to obtain the compound of interest as a pale yellow oil substance (1.73 g, 32%, E/Z mixture).

$^1$H-NMR (400 MHz, CDCl$_3$): δ ppm:

Major isomer: 1.45 (9H, S), 2.29-2.35 (1H, m), 2.62-2.71 (2H, m), 2.89-2.98 (1H, m), 3.27-3.35 (1H, m), 3.92 (1H, broad), 5.47-5.49 (1H, m), 5.80-5.87 (2H, m).

Minor isomer: 1.49 (9H, s), 2.42-2.48 (1H, m), 2.62-2.71 (2H, m), 2.89-2.98 (2H, m), 4.34-4.36 (1H, m), 5.37-5.38 (1H, m), 5.61-5.64 (2H, m).

(1-c) Tert-butyl [6-(nitromethyl)bicyclo[3.2.0]hept-3-en-6-yl]acetate

Tert-butyl bicyclo[3.2.0]hept-3-en-6-ylideneacetate (1.73 g, 8.39 mmol) was dissolved in nitromethane (10 mL). To the solution, 1,8-diazabicyclo[5.4.0]undec-7-ene (1.3 mL, 8.4 mmol) was added, and the mixture was stirred at room temperature for 1 hour and then heated with stirring at 50 to 60° C. for 5 hours. The mixture was allowed to cool and then diluted with 1 N hydrochloric acid and saturated saline, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.98 g, 89%).

$^1$H-NMR (400 MHz, CDCl$_3$): δ ppm: 1.45 (9H, s), 1.53 (1H, dd, J=7.5, 12.9 Hz), 2.17 (1H, d, J=15.2 Hz), 2.31 (1H, ddd, J=2.4, 8.6, 12.1 Hz), 2.47 (2H, s), 2.52-2.58 (1H, m), 2.87 (1H, quint, J=7.5 Hz), 3.25-2.66 (1H, m), 4.78 (1H, d, J=11.4 Hz), 4.87 (1H, d, J=11.4 Hz), 5.65-5.67 (1H, m), 5.95 (1H, dd, J=1.6, 5.9 Hz).

(1-d) Tert-butyl [6-(aminomethyl)bicyclo[3.2.0]hept-3-en-6-yl]acetate

Tert-butyl [6-(nitromethyl)bicyclo[3.2.0]hept-3-en-6-ylacetate] (1.98 g, 7.41 mmol) was dissolved in ethanol (20 mL) and water (10 mL). To the solution, iron powder (2.07 g, 37.0 mmol) and ammonium chloride (392.7 mg, 7.41 mmol) were added, and the mixture was stirred for 4.5 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate. Then, the solvent was distilled off under reduced pressure to obtain the compound of interest as a pale yellow solid (1.99 g, this compound was used directly in the next reaction without being purified).

$^1$H-NMR (400 MHz, CDCl$_3$): δ ppm: 1.39-1.49 (1H, m), 1.44 (9H, s), 1.97 (1H, ddd, J=2.8, 9.0, 11.7 Hz), 2.14 (1H, dd, J=2.3, 16.8 Hz), 2.25 (1H, d, J=13.7 Hz), 2.32 (1H, d, J=13.7 Hz), 2.47-2.55 (1H, m), 2.75 (1H, quint, J=7.4 Hz), 2.88 (2H, s), 2.98-2.99 (1H, m), 5.77-5.79 (1H, m), 5.87-5.89 (1H, (1-e) [6-(Aminomethyl)bicyclo[3.2.0]hept-3-en-6-yl]acetic acid A 4 N solution of hydrochloric acid in ethyl acetate (10 mL) was added to tert-butyl [6-(aminomethyl)bicyclo[3.2.0]hept-3-en-6-yl]acetate (0.99 g, 4.17 mmol), and the mixture was stirred at room temperature for 1 hour. Then, the solvent was distilled off under reduced pressure. The residue was suspended by the addition of dichloromethane. To the suspension, triethylamine was then added dropwise, and the resulting powder was collected by filtration. The obtained powder was washed with dichloromethane and then dried under reduced pressure to obtain the compound of interest as a white powder (211.6 mg, 35%).

$^1$H-NMR (400 MHz, CDCl$_3$): δ ppm: 1.49 (1H, dd, J=7.6, 12.5 Hz), 2.06 (1H, ddd, J=2.6, 7.6, 12.5 Hz), 2.17 (1H, dd, J=2.6, 16.8 Hz), 2.49 (2H, s), 2.48-2.56 (1H, m), 2.86 (1H, quint, J=7.6 Hz), 3.15-3.16 (1H, m), 3.18 (1H, d, J=12.7 Hz), 3.22 (1H, d, J=12.7 Hz), 5.75-5.78 (1H, m), 5.91-5.93 (1H, m).

Production Example 2

[6-(Aminomethyl)bicyclo[3.2.0]hept-3-en-6-yl]acetic acid hydrochloride

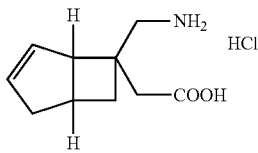

Water (5 mL) and a 4 N solution of hydrochloric acid in 1,4-dioxane (22 mL) were added to 6-(aminomethyl)bicyclo[3.2.0]hept-3-en-6-yl]acetic acid (320.2 mg, 1.77 mmol), and the mixture was stirred at room temperature for 5 minutes. The solvent was distilled off under reduced pressure. To the residue, 1,4-dioxane was added, and the mixture was heated and then allowed to cool to room temperature. The resulting powder was collected by filtration. The obtained powder was washed with 1,4-dioxane and then dried to obtain the compound of interest as a white powder (350.0 mg, 92%).

$^1$H-NMR (400 MHz, CD$_3$OD): δ ppm: 1.51 (1H, dd, J=7.6, 12.7 Hz), 2.16 (1H, ddd, J=2.8, 7.6, 15.6 Hz), 2.19 (1H, dd, J=2.2, 16.8 Hz), 2.51 (2H, s), 2.53-2.59 (1H, m), 2.89 (1H, quint, J=7.6 Hz), 3.18-3.19 (1H, m), 3.33 (1H, d, J=13.3 Hz), 3.37 (1H, d, J=13.3 Hz), 5.70-5.73 (1H, m), 5.97-6.00 (1H, m).

Production Example 3

[6-(Aminomethyl)bicyclo[3.2.0]hept-3-en-6-yl]acetic acid benzenesulfonate

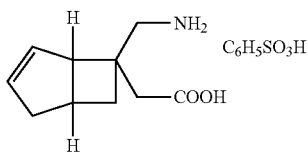

6-(Aminomethyl)bicyclo[3.2.0]hept-3-en-6-yl]acetic acid (152.2 g, 391 mmol) was dissolved in 2-propanol (7.5 mL) and water (2.6 mL). To the solution, benzenesulfonic acid monohydrate (305.2 mg, 1.73 mmol) was then added, and the mixture was stirred at room temperature for 5 minutes. The solvent was distilled off under reduced pressure, followed by further azeotropic dehydration with 2-propanol. Then, the residue was washed with 2-propanol to obtain the compound of interest as a white powder (260.4 mg, 55%).

$^1$H-NMR (400 MHz, CD$_3$OD): δ ppm: 1.51 (1H, dd, J=7.4, 12.7 Hz), 2.12-2.21 (2H, m), 2.51 (2H, s), 2.51-2.59 (1H, m), 2.89 (1H, quint, J=7.4 Hz), 3.17-3.18 (1H, m), 3.32 (1H, d, J=13.3 Hz), 3.36 (1H, d, J=13.3 Hz), 5.69-5.71 (1H, m), 5.97-6.00 (1H, m), 7.40-7.46 (3H, m), 7.80-7.84 (2H, m).

Production Example 4

[6-Aminomethyl-3-methylbicyclo[3.2.0]hept-3-en-6-yl]acetic acid

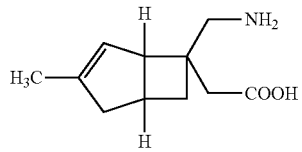

(4-a) Methyl 4-methyl-3-hydroxyhept-6-enoate

Sodium hydride (>63% oil, 1.64 g, 43.1 mmol) was added to a solution of methyl 3-oxopentanoate (5.10 g, 39.2 mmol) in tetrahydrofuran (50 mL) under ice cooling, and the mixture was stirred in this state for 10 minutes. To the reaction solution, n-butyllithium (1.66 M solution in hexane, 25.9 mL, 43.1 mmol) was added dropwise, and the mixture was further stirred for 10 minutes under ice cooling. Then, allyl bromide (5.18 g, 43.1 mmol) was added thereto, and the mixture was stirred in this state for 30 minutes and then further stirred overnight at room temperature. To the reaction solution, 1 N hydrochloric acid and saturated saline were added, followed by extraction with diethyl ether. The organic layer was washed with saturated saline and dried over anhydrous magnesium sulfate, and the solvent was distilled off under reduced pressure. The obtained residue was dissolved in methanol (100 mL). To the solution, sodium borohydride (1.89 g, 50 mmol) was added under ice cooling, and the mixture was stirred in this state for 1.5 hours. 2 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (5.72 g, 85%, mixture of diastereomers).

$^1$H-NMR (400 MHz, CDCl$_3$): δ ppm: 0.89-0.94 (3H, m), 1.58-1.75 (1H, m), 1.91-2.03 (1H, m), 2.21-2.33 (1H, m), 2.43-2.56 (2H, m), 3.72 (3H, s), 3.84-4.00 (1H, m), 5.01-5.07 (2H, m), 5.74-5.84 (1H, m).

(4-b) 4-Methyl-3-hydroxyhept-6-enoic acid

Methyl 4-methyl-3-hydroxyhept-6-enoate (5.72 g, 33.2 mmol) was dissolved in a 2 N solution of potassium hydroxide in methanol (50 mL), and the solution was stirred overnight at room temperature. From the reaction solution, the solvent was distilled off under reduced pressure. To the residue, a 1 N aqueous sodium hydroxide solution was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a yellow oil substance (2.21 g, 42%, mixtures of diastereomers).

$^1$H-NMR (400 MHz, CDCl$_3$): δ ppm: 0.90-0.94 (3H, m), 1.64-1.74 (1H, m), 1.93-2.00 (1H, m), 2.24-2.32 (1H, m), 2.45-2.61 (2H, m), 3.87-4.03 (1H, m), 5.03-5.08 (2H, m), 5.75-5.83 (1H, m).

(4-c) Tert-butyl 3-methylbicyclo[3.2.0]hept-3-en-6-ylideneacetate

4-Methyl-3-hydroxyhept-6-enoic acid (2.21 g, 13.9 mmol) was dissolved in acetic anhydride (14 mL). To the solution, potassium acetate (3.29 g, 33.4 mmol) was added, and the mixture was stirred at room temperature for 2 hours. The reaction solution was heated to 110 to 120° C. and stirred for 3.5 hours. To the reaction solution, ice water and toluene were then added, and this mixture was stirred at room temperature for 1 hour. The mixture was separated into aqueous and organic layers by the addition of saturated saline and toluene. Then, the organic layer was washed with a 1 N aqueous sodium hydroxide solution and saturated saline in this order, then dried over anhydrous magnesium sulfate, and then filtered. The filtrate was added to a reaction solution prepared by adding sodium hydride (>63% oil, 533.3 mg, 14.0 mmol) to a solution of tert-butyl dimethoxyphosphorylacetate (3.24 g, 14.5 mmol) in tetrahydrofuran (20 mL) under ice cooling, and the mixture was further stirred for 1.5 hours. The reaction solution was separated into aqueous and organic layers by the addition of a saturated aqueous solution of ammonium chloride and saturated saline. The aqueous layer was subjected to extraction with ethyl acetate. The organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.21 g, 40%, E/Z mixture).

$^1$H-NMR (400 MHz, CDCl$_3$): δ ppm:

Major isomer: 1.45 (9H, s), 2.11-2.22 (4H, m), 2.59-2.71 (2H, m), 2.87-2.97 (1H, m), 3.26-3.34 (1H, m), 3.87 (1H, broad), 5.22-5.23 (1H, m), 5.45-5.47 (1H, m).

Minor isomer: 1.49 (9H, s), 2.11-2.21 (4H, m), 2.43-2.46 (1H, m), 2.59-2.70 (1H, m), 2.75-2.83 (1H, m), 2.87-2.97 (1H, m), 4.29 (1H, broad), 5.36 (1H, s), 5.59 (1H, s).

(4-d) Tert-butyl [3-methyl-6-(nitromethyl)bicyclo [3.2.0]hept-3-en-6-yl]acetate

Tert-butyl 3-methylbicyclo[3.2.0]hept-3-en-6-ylideneacetate (1.21 g, 5.50 mmol) was dissolved in nitromethane (7 mL). To the solution, 1,8-diazabicyclo[5.4.0]undec-7-ene (0.91 mL, 6.0 mmol) was added, and the mixture was heated with stirring at 50 to 60° C. for 6 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.14 g, 74%).

$^1$H-NMR (400 MHz, CDCl$_3$): δ ppm: 1.45 (9H, s), 1.53 (1H, dd, J=7.6, 12.9 Hz), 1.80 (3H, s), 2.04 (1H, d, J=16.4 Hz), 2.29 (1H, ddd, J=2.8, 7.6, 12.9 Hz), 2.47 (2H, s), 2.49 (1H, dd, H=7.6, 16.4 Hz), 2.86 (1H, quint, J=7.6 Hz), 3.21-3.22 (1H, m), 4.74 (1H, d, J=11.7 Hz), 4.84 (1H, J=11.7 Hz), 5.25 (1H, s).

(4-e) Tert-butyl [6-aminomethyl-3-methylbicyclo [3.2.0]hept-3-en-6-yl]acetate

Tert-butyl [3-methyl-6-(nitromethyl)bicyclo[3.2.0]hept-3-en-6-yl]acetate (1.12 g, 3.99 mmol) was dissolved in ethanol (20 mL) and water (10 mL). To the solution, iron powder (892.8 mg, 15.9 mmol) and ammonium chloride (211.5 mg, 3.99 mmol) were added, and the mixture was stirred for 4 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline, then dried over anhydrous magnesium sulfate, and the solvent was then distilled off under reduced pressure. To the residue, a 4 N solution of hydrochloric acid in ethyl acetate (5 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (105.8 mg, 28%).

$^1$H-NMR (400 MHz, CD$_3$OD): δ ppm: 1.40 (1H, dd, J=7.6, 12.3 Hz), 1.79 (3H, s), 2.02-2.08 (2H, m), 2.43-2.50 (1H, m), 2.45 (1H, d, J=16.2 Hz), 2.51 (1H, d, J=16.2 Hz), 2.85 (1H, quint, J=7.6 Hz), 3.05-3.12 (1H, m), 3.13 (1H, d, J=13.0 Hz), 3.17 (1H, d, J=13.0 Hz), 5.36 (1H, t, J=1.6 Hz).

Production Example 5

[6-Aminomethyl-3-ethylbicyclo[3.2.0]hept-3-en-6-yl]acetic acid

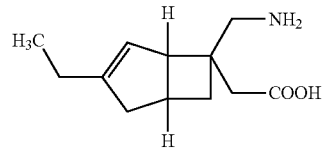

(5-a) Ethyl 4-ethyl-3-hydroxyhept-6-enoate

Sodium hydride (>63% oil, 2.09 g, 55 mmol) was added to a solution of ethyl 3-oxohexanoate (7.91 g, 50 mmol) in tetrahydrofuran (50 mL) under ice cooling, and the mixture was stirred in this state for 10 minutes. To the reaction solution, n-butyllithium (1.58 M solution in hexane, 34.8 mL, 55 mmol) was added dropwise, and the mixture was further stirred for 10 minutes under ice cooling. Then, allyl bromide (4.7 mL, 55 mmol) was added thereto, and the mixture was stirred in this state for 1 hour and then further stirred at room temperature for 4 hours. To the reaction solution, 1 N hydrochloric acid and a saturated aqueous solution of ammonium chloride were added, followed by extraction with n-pentane. The organic layer was washed with saturated saline and dried over anhydrous magnesium sulfate, and the solvent was distilled off under reduced pressure. The obtained residue was dissolved in ethanol (80 mL). To the solution, sodium borohydride (1.51 g, 40 mmol) was added under ice cooling, and the mixture was stirred in this state for 2 hours. 1 N hydrochloric acid (50 mL) was added thereto, and the mixture was stirred for 30 minutes. Then, saturated saline was added thereto, followed by extraction with ethyl acetate. The organic layer was washed with saturated saline and then dried over anhydrous magnesium sulfate, and the solvent was distilled off under reduced pressure. The residue was purified by silica gel column chromatography to obtain the compound of interest as a pale yellow oil substance (3.64 g, 37%, mixture of diastereomers).

$^1$H-NMR (400 MHz, CDCl$_3$): δ ppm: 0.91 (3H, t, J=7.5 Hz), 1.28 (3H, t, J=7.2 Hz), 1.43-1.55 (2H, m), 1.98-2.28 (2H, m), 2.45-2.48 (2H, m), 2.88-2.93 (1H, m), 4.07-4.10 (1H, m), 4.10-4.20 (2H, m), 5.01-5.09 (2H, m), 5.75-5.86 (1H, m).

(5-b) 4-Ethyl-3-hydroxyhept-6-enoic acid

Ethyl 4-ethyl-3-hydroxyhept-6-enoate (3.64 g, 18.2 mmol) was dissolved in a 2 N solution of potassium hydroxide in methanol (120 mL), and the solution was stirred overnight at room temperature. From the reaction solution, the solvent was distilled off under reduced pressure. To the residue, a 1 N aqueous sodium hydroxide solution (200 mL) was then added, followed by extraction with diethyl ether. The aqueous layer was made acidic by the addition of concentrated hydrochloric acid under ice cooling, followed by extraction with diethyl ether again. The organic layer was washed with saturated saline and dried over anhydrous magnesium sulfate. Then, the solvent was distilled off under reduced pressure to obtain the compound of interest as a pale yellow oil substance (3.14 g, <100%, mixture of diastereomers).

$^1$H-NMR (400 MHz, CDCl$_3$): δ ppm: 0.91-0.96 (3H, m), 1.39-1.52 (3H, m), 2.01-2.28 (2H, m), 2.52-2.55 (2H, m), 4.05-4.15 (2H, m), 5.03-5.10 (2H, m), 5.74-5.86 (1H, m).

(5-c) Tert-butyl 3-ethylbicyclo[3.2.0]hept-3-en-6-ylideneacetate

4-Ethyl-3-hydroxyhept-6-enoic acid (3.13 g, 18.2 mmol) was dissolved in acetic anhydride (15 mL). To the solution, potassium acetate (4.27 g, 43.6 mmol) was added, and the mixture was stirred at room temperature for 100 minutes. The reaction solution was heated to reflux and stirred for 3.5 hours to form "3-ethylbicyclo[3.2.0]hept-6-en-6-one" in the reaction solution. To the reaction solution, ice water and toluene were then added, and this mixture was stirred overnight at room temperature. The mixture was separated into aqueous and organic layers by the addition of saturated saline (50 mL) and toluene (20 mL). Then, the organic layer was washed with a 1 N aqueous sodium hydroxide solution and saturated saline in this order, then dried over anhydrous magnesium sulfate, and filtered. The filtrate was added to a reaction solution prepared by adding sodium hydride (>65% oil, 761.9 mg, 20 mmol) to a solution of tert-butyl dimethoxyphosphorylacetate (4.48 g, 20 mmol) in tetrahydrofuran (50 mL) under ice cooling, and the mixture was further stirred for 1 hour. The reaction solution was separated into aqueous and organic layers by the addition of a saturated aqueous solution of ammonium chloride and saturated saline. The aqueous layer was subjected to extraction with ethyl acetate. The organic layers were combined, then washed with saturated saline, and then dried over anhydrous magnesium sulfate. The solvent was distilled off under reduced pressure, and the residue was purified by silica gel column chromatography to obtain the compound of interest as a pale yellow oil substance (1.32 g, 31%, E/Z mixture).

$^1$H-NMR (400 MHz, CDCl$_3$): δ ppm:

Major isomer: 1.06 (3H, t, J=7.4 Hz), 1.45 (9H, s), 2.07-2.22 (3H, m), 2.59-2.70 (2H, m), 2.87-2.96 (1H, m), 3.30 (1H, ddt, J=8.6, 18.4, 2.7 Hz), 3.86-3.88 (1H, m), 5.22-5.23 (1H, m), 5.45-5.47 (1H, m).

Minor isomer: 1.08 (3H, t, J=7.3 Hz), 1.49 (9H, s), 2.07-2.21 (3H, m), 2.43-2.47 (1H, m), 2.59-2.70 (1H, m), 2.75-2.85 (1H, m), 2.87-2.96 (1H, m), 4.28-4.31 (1H, m), 5.35-5.38 (1H, m), 5.45-5.47 (1H, m).

(5-d) Tert-butyl [3-ethyl-6-(nitromethyl)bicyclo [3.2.0]hept-3-en-6-yl]acetate

Tert-butyl [3-ethylbicyclo[3.2.0]hept-3-en-6-ylideneacetate (1.32 g, 5.63 mmol) was dissolved in nitromethane (7 mL). To the solution, 1,8-diazabicyclo[5.4.0]undec-7-ene (1.2 mL, 7.3 mmol) was added, and the mixture was heated with stirring at 50 to 60° C. for 7 hours. The mixture was allowed to cool, and a saturated aqueous solution of potassium dihydrogen phosphate was then added thereto, followed by extraction with ethyl acetate. Then, the organic layer was dried over anhydrous magnesium sulfate, and the solvent was distilled off under reduced pressure. The residue was purified by silica gel column chromatography to obtain the compound of interest as a colorless oil substance (1.39 g, 84%).

$^1$H-NMR (400 MHz, CDCl$_3$): δ ppm: 1.09 (3H, t, J=7.4 Hz), 1.46 (9H, s), 1.52 (1H, dd, J=7.6, 13.2 Hz), 2.06 (1H, d, 16.6 Hz), 2.14 (2H, q, J=7.4 Hz), 2.30 (1H, ddd, J=2.4, 7.6, 13.2 Hz), 2.47 (2H, s), 2.49 (1H, dd, J=7.6, 16.6 Hz), 2.86 (1H, quint, J=7.6 Hz), 3.21-3.22 (1H, m), 4.75 (1H, d, J=11.7 Hz), 4.84 (1H, d, J=11.7 Hz), 5.27 (1H, s).

(5-e) [6-Aminomethyl-3-ethylbicyclo[3.2.0]hept-3-en-6-yl]acetic acid

Tert-butyl [3-ethyl-6-(nitromethyl)bicyclo[3.2.0]hept-3-en-6-yl]acetate (1.09 g, 4.71 mmol) was dissolved in ethanol (10 mL) and water (5 mL). To the solution, iron powder (1.32 g, 23.5 mmol) and ammonium chloride (249.6 mg, 4.71 mmol) were added, and the mixture was stirred for 2 hours under heating to reflux. The mixture was allowed to cool, then diluted with saturated saline, a saturated aqueous solution of sodium bicarbonate, and ethyl acetate, and filtered through Celite to remove insoluble matter. The filtrate was separated into organic and aqueous layers. The organic layer was washed with saturated saline and then dried over anhydrous magnesium sulfate, and the solvent was then distilled off under reduced pressure. To the residue, a 4 N solution of hydrochloric acid in ethyl acetate (20 mL) was added, and the mixture was stirred at room temperature for 1 hour. Then, the solvent was distilled off under reduced pressure. The residue was suspended in dichloromethane. To the suspension, triethylamine was added dropwise, and the resulting powder was collected by filtration, then washed with dichloromethane, and then dried to obtain the compound of interest as a white powder (425.1 mg, 43%).

$^1$H-NMR (400 MHz, CD$_3$OD): δ ppm: 1.10 (3H, t, J=7.4 Hz), 1.48 (1H, dd, J=7.5, 12.5 Hz), 2.03-2.08 (2H, m), 2.14 (2H, q, J=7.4 Hz), 2.46 (1H, d, J=16.2 Hz), 2.46-2.53 (1H, m), 2.51 (1H, d, J=16.2 Hz), 2.85 (1H, quint, J=7.5 Hz), 3.09-3.10 (1H, m), 3.14 (1H, d, J=13.0 Hz), 3.18 (1H, d, J=13.0 Hz), 5.38 (1H, dd, J=1.7, 3.7 Hz).

Production Example 6

[6-Aminomethyl-3-ethylbicyclo[3.2.0]hept-3-en-6-yl]acetic acid p-toluenesulfonate

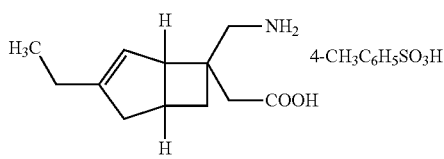

Tert-butyl [6-(tert-butoxycarbonylamino)methyl-3-ethylbicyclo[3.2.0]hept-3-en-6-yl]acetate (1152.23 g, 391.6 mmol) was dissolved in benzene (1.2 L). To the solution, thioanisole (145.57 g, 1173 mmol) and p-toluenesulfonic acid monohydrate (89.39 g) were then added, and the mixture was stirred for 2 hours under reflux. The mixture was left standing overnight at room temperature, and the resulting powder was collected by filtration. The obtained powder was washed with ethyl acetate and then dried to obtain the compound of interest as a white powder (88.29 g, 59%).

$^1$H-NMR (400 MHz, CD$_3$OD): δ ppm: 1.11 (3H, t, J=7.4 Hz), 1.51 (1H, dd, 7.4, 12.7 Hz), 2.06-2.20 (4H, m), 2.37 (3H, s), 2.49-2.56 (1H, m), 2.51 (2H, s), 2.87 (1H, quint, J=7.4 Hz), 3.12-3.14 (1H, m), 3.28 (1H, d, J=13.5 Hz), 3.33 (1H, d, J=13.5 Hz), 5.31-5.32 (1H, m), 7.21-7.25 (2H, m), 7.69-7.72 (2H, m).

Production Example 7

[6-(Aminomethyl)-3-ethylbicyclo[3.2.0]hept-3-en-6-yl]acetic acid benzenesulfonate

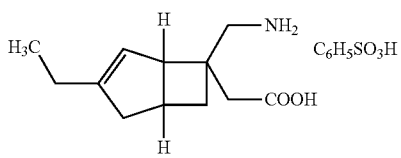

6-(Aminomethyl)-3-ethylbicyclo[3.2.0]hept-3-en-6-yl] acetic acid (4.50 g, 20.6 mmol) was dissolved by heating in a 1 M aqueous benzenesulfonic acid monohydrate solution (22.7 mL), and the solution was then allowed to cool to room temperature. The resulting solid was collected by filtration. The solid was washed with water (15 mL) and then dried using a vacuum pump to obtain the compound of interest as a colorless solid (6.45 g, 77%).

$^1$H-NMR (400 MHz, CD$_3$OD): δ ppm: 1.11 (3H, t, J=7.4 Hz), 1.50 (1H, dd, J=7.5, 12.6 Hz), 2.08 (1H, d, 16.5 Hz), 2.10-2.20 (3H, m), 2.46-2.56 (3H, m), 2.87 (1H, quint. J=7.5 Hz), 3.12-3.13 (1H, m), 3.28 (1H, d, J=13.4 Hz), 3.33 (1H, d, J=13.4 Hz), 5.31 (1H, d, J=1.8 Hz), 7.39-7.45 (3H, m), 7.80-7.85 (2H, m).

Step of Reducing Nitro Group

Production Example 8

Tert-butyl [6-aminomethyl-3-ethylbicyclo[3.2.0]hept-3-en-6-yl]acetate (i)

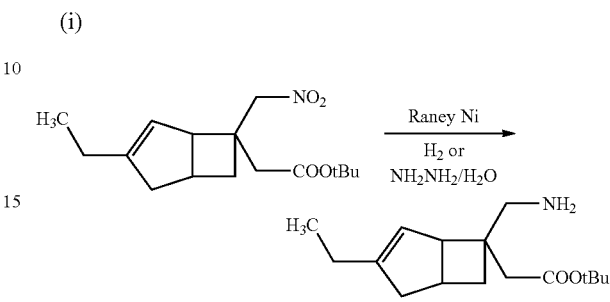

Raney nickel (102.3 g, 0.15 w/w) and ethanol (5.5 L, 8.0 v/w) were added to tert-butyl [3-ethyl-6-(nitromethyl)bicyclo[3.2.0]hept-3-en-6-yl]acetate (709.0 g, net: 681.8 g, 2.31 mol, 85:15 diastereomeric mixture), and the mixture was stirred. To the reaction solution, hydrazine monohydrate (458.0 ml, 9.23 mol, 4.00 eq.) was added, and the mixture was stirred at 40° C. for 2 hours. The mixture was cooled to room temperature, and the Raney nickel was filtered off. Then, the solvent was distilled off to obtain the compound of interest as a brown oil substance (637.0 g, net: 552.3 g, yield: 90.2%, 85:15 diastereomeric mixture).

$^1$H-NMR (400 MHz, CDCl$_3$): δ ppm: 1.05-1.10 (each t), 1.44-1.61 (m), 1.86-2.38 (m), 2.42-2.55 (m), 2.73-3.05 (m), 5.40-5.48 (m).

(ii)

Raney nickel (96 mg, 0.16 w/w) and ethanol (200 μL) were added to tert-butyl [3-ethyl-6-(nitromethyl)bicyclo[3.2.0]hept-3-en-6-yl]acetate (59 mg, 85:15 diastereomeric mixture), and the mixture was stirred at room temperature for 12 hours under the hydrogen atmosphere. The Raney nickel was filtered off. Then, the solvent was distilled off to obtain the compound of interest as a brown oil substance (49 mg, yield: 92%, 85:15 diastereomeric mixture).

Production Example 9

Tert-butyl [6-(aminomethyl)bicyclo[3.2.0]hept-3-en-6-yl]acetate

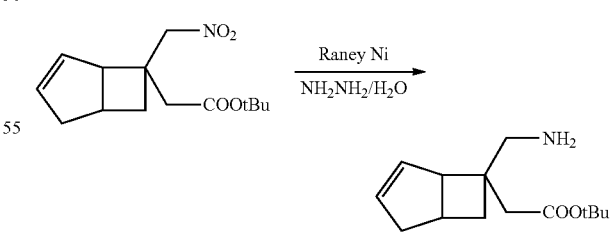

Raney nickel (0.4 g) and ethanol (24 ml) were added to tert-butyl [6-(nitromethyl)bicyclo[3.2.0]hept-3-en-6-yl]acetate (4.0 g, 90:10 diastereomeric mixture), and the mixture was stirred. To the reaction solution, hydrazine monohydrate (2.9 ml) was added, and the mixture was stirred for 0.5 hours. The consumption of the starting materials was confirmed by thin-layer chromatography, and the Raney nickel was then filtered off. The solvent was distilled off to obtain the compound of interest as a brown oil substance (3.62 g, 90:10 diastereomeric mixture).

Thin-layer chromatography developer: hexane:ethyl acetate=9:1

Rf value of nitro form: 0.7, Rf value of reduced form: 0.1 (with tailing)

$^1$H-NMR (400 MHz, CDCl$_3$): δ ppm: 1.44-1.51 (m), 1.93-2.17 (m), 2.23-2.35 (m), 2.48-2.60 (m), 2.70-2.90 (m), 2.95-3.30 (m), 5.75-5.80 (m), 5.83-5.90 (m).

Production Example 10

Tert-butyl [6-aminomethyl-3-methylbicyclo[3.2.0]hept-3-en-6-yl]acetate

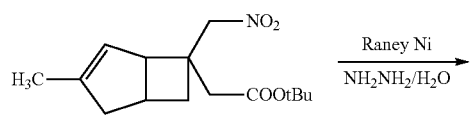

Raney nickel (0.28 g) and ethanol (20 ml) were added to tert-butyl [6-(nitromethyl)-3-methylbicyclo[3.2.0]hept-3-en-6-yl]acetate (2.81 g, 90:10 diastereomeric mixture), and the mixture was stirred. To the reaction solution, hydrazine monohydrate (1.9 ml) was added, and the mixture was stirred for 0.75 hours. The consumption of the starting materials was confirmed by thin-layer chromatography, and the Raney nickel was then filtered off. The solvent was distilled off to obtain the compound of interest as a brown oil substance (2.50 g, 90:10 diastereomeric mixture).

Thin-layer chromatography developer: hexane:ethyl acetate=9:1

Rf value of nitro form: 0.7, Rf value of reduced form: 0.1 (with tailing)

$^1$H-NMR (400 MHz, CDCl$_3$): δ ppm: 1.44-1.61 (m), 1.80-1.90 (m), 1.93-2.06 (m), 2.10-2.20 (m), 2.23-2.38 (m), 2.40-2.60 (m), 2.73-2.90 (m), 2.92-3.30 (m), 5.40-5.45 (m).

Step of Resolving Diastereomers

Production Example 11

Tert-butyl [(1R*,5S*,6S*)-6-aminomethyl-3-ethylbicyclo[3.2.0]hept-3-en-6-yl]acetate p-toluenesulfonate

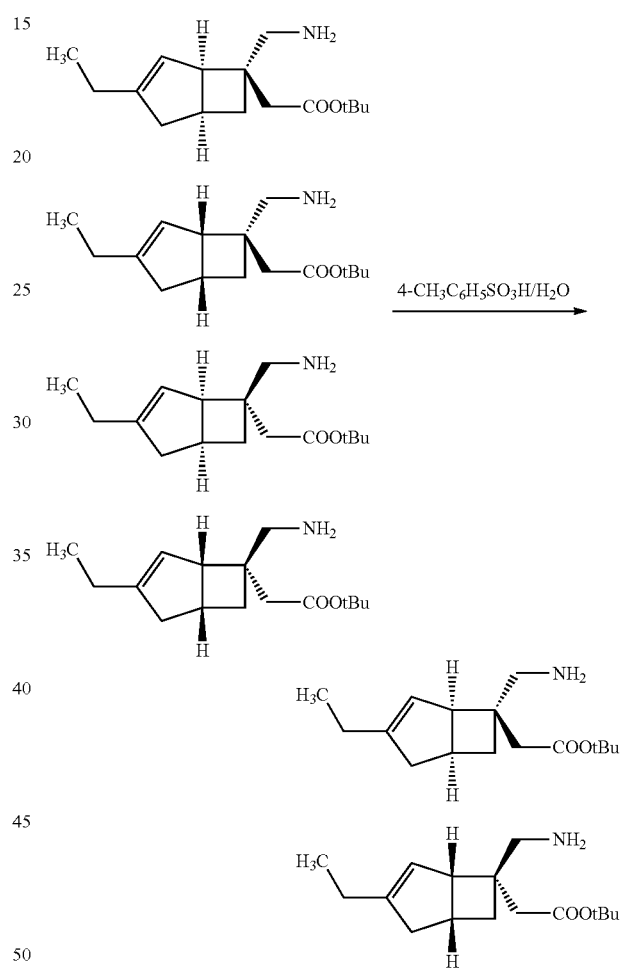

Ethyl acetate (70 ml, 10.4 v/w) was added to tert-butyl [6-aminomethyl-3-ethylbicyclo[3.2.0]hept-3-en-6-yl]acetate (7.8 g, purity: 86.7%, 22.03 mmol, 87:13 diastereomeric mixture), and the mixture was stirred at room temperature. After addition of p-toluenesulfonic acid monohydrate (4.2 g, 22.03 mmol, 0.87 eq.), the mixture was stirred at room temperature for 3 hours, and a crystal was collected by filtration. Then, the crystal was dried under reduced pressure under the condition of 40° C. to obtain tert-butyl [(1R*,5S*,6S*)-6-aminomethyl-3-ethylbicyclo[3.2.0]hept-3-en-6-yl]acetate p-toluenesulfonate as a white crystal (7.8 g, yield: 80.6%, diastereomeric ratio: 99.7:0.3).

$^1$H-NMR (400 MHz, DMSO-d6): δ ppm: 1.04 (3H, t, J=7.4 Hz), 1.31-1.40 (1H, m), 1.40 (9H, s), 1.98-2.15 (4H, m), 2.25 (3H, s), 2.25-2.50 (3H, m), 2.76 (1H, quint, J=7.4 Hz), 3.05-

3.18 (3H, m), 3.35 (1H, br s), 5.20-5.22 (1H, m), 7.10-7.12 (2H, m), 7.45-7.48 (2H, m), 7.74 (1H, br s).

Anal. calcd for $C_{23}H_{35}NO_5S$: C, 63.13; H, 8.06; N, 3.20; S, 7.33. Found C, 63.10; H, 8.14; N, 3.29; S, 7.30.

GC Analysis Conditions (Diastereomeric Ratio Measurement)

Column: CP-Sil 8CB for Amine (GL Science, 30 m×0.25 mm, 0.25 μm)

Detector: FID

Temperature: column oven (130° C.), injection (250° C.), detector (250° C.)

Temperature conditions: (i) 130° C. (5.5 min), (ii) 130-270° C. (10° C./min), (iii) 270° C. (4.5 min)

Flow rate: 1.5 ml/min (average linear velocity: 38 cm/sec)

Split ratio: 1/10

Carrier gas: helium

Analysis time: 25 min

Peak cut: 0.0-2.0 min

Retention time: 13.8 min, 14.0 min

Optical Resolution Step

Production Example 12

Tert-butyl [(1R,5S,6S)-6-aminomethyl-3-ethylbicyclo[3.2.0]hept-3-en-6-yl]acetate carboxylate (optically active carboxylate)

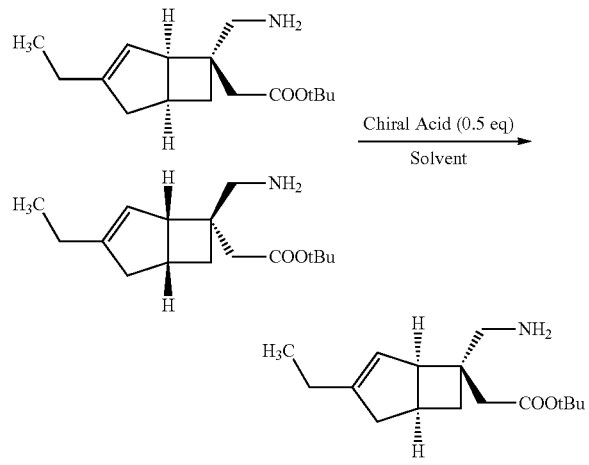

Tert-butyl [(1R*,5S*,6S*)-6-aminomethyl-3-ethylbicyclo[3.2.0]hept-3-en-6-yl]acetate p-toluenesulfonate was suspended in ethyl acetate (20 v/w). The suspension was separated into aqueous and organic layers by the addition of an aqueous sodium bicarbonate solution (4 v/w) to obtain the free form of tert-butyl [(1R*,5S*,6S*)-6-aminomethyl-3-ethylbicyclo[3.2.0]hept-3-en-6-yl]acetate. To this tert-butyl [(1R*,5S*,6S*)-6-aminomethyl-3-ethylbicyclo[3.2.0]hept-3-en-6-yl]acetate (200 mg, 0.754 mmol), diisopropyl ether (IPE) or acetonitrile (MeCN) (1.0 mL, 5.0 v/w), and then optically active carboxylic acid (0.5 eq.) were added, and the mixture was stirred at room temperature. The deposited crystal was filtered and washed with the solvent (0.5 mL, 2.5 v/w) used. The obtained crystal was dried under reduced pressure to obtain the corresponding salt form at the yield and optical purity shown in Table 1 below.

The optical purity was analyzed by converting the obtained salt into the free form with an aqueous sodium bicarbonate solution and then derivatizing the free form into a 3,5-dinitrobenzoyl form.

HPLC analysis conditions (optical purity measurement, analyzed after derivatization into 3,5-dinitrobenzoyl form)

Column: CHIRALPAK AS-RH×2 (Daisel, 4.6 mm×150 mm, 5 μm)

Detection: 220 nm, Column temperature: 40° C., Flow rate: 0.8 ml/min

Mobile phase: MeCN/5 mM phosphate buffer (pH 7.0) =55/45

Retention time: 29.6 min, 31.8 min, 36.1 min

TABLE 1

| | | IPE | | MeCN | |
|---|---|---|---|---|---|
| Entry | Chiral Acid | Yield (%) | e.e. (%) | Yield (%) | e.e. (%) |
| 1 | D-Mandelic Acid | 42.1 | 64.3 (1R) | 32.4 | 96.1 (1R) |
| 2 | L-Mandelic Acid | 42.8 | 59.2 (1S) | 30.4 | 97.3 (1S) |
| 3 | Di-p-toluoyl-L-tartaric Acid | 15.2 | 66.8 (1R) | 26.6 | 26.1 (1R) |
| 4 | N-Boc-L-Proline | 33.6 | 56.9 (1R) | 36.4 | 48.7 (1R) |
| 5 | (R)-α-Methoxyphenylacetic Acid | 47.2 | 48.0 (1R) | 45.2 | 52.5 (1R) |
| 6 | O-Acetyl-L-Mandelic Acid | 46.7 | 44.9 (1S) | 41.5 | 56.1 (1S) |
| 7 | Di-benzoyl-L-tartaric Acid | 11.8 | 41.9 (1R) | 21.4 | 8.2 (1R) |
| 8 | O-Acetyl-D-Mandelic Acid | 47.2 | 35.9 (1R) | 42.2 | 53.8 (1R) |
| 9 | N-Boc-L-Alanine | 40.0 | 18.2 (1R) | 30.7 | 61.3 (1R) |

Step of Performing Optical Resolution from Diastereomeric Mixture

Example 1

Tert-butyl [(1R,5S,6S)-6-aminomethyl-3-ethylbicyclo[3.2.0]hept-3-en-6-yl]acetate D-mandelate

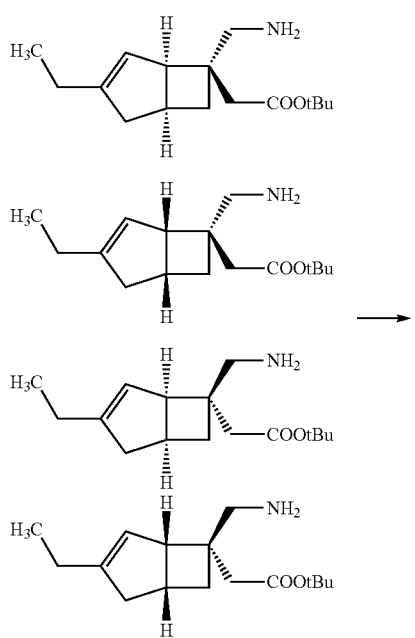

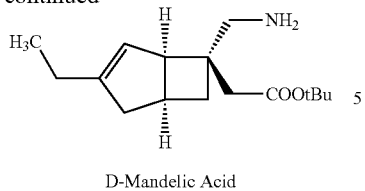

D-Mandelic Acid

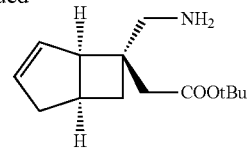

(S)—O—Acetyl Mandelic Acid

Acetonitrile (4.7 L, 8.6 v/w) was added to tert-butyl [6-aminomethyl-3-ethylbicyclo[3.2.0]hept-3-en-6-yl]acetate (627.0 g, net: 543.6 g, 2.05 mol, 85:15 diastereomeric mixture), and the mixture was stirred at 40° C. To the reaction solution, D-mandelic acid (116.3 g, 0.76 mmol, 0.37 eq.) was added, and the mixture was stirred at 40° C. for 1 hour and then allowed to cool slowly to 3° C. After stirring at 3° C. for 1 hour, the resulting crystal was collected by filtration. Then, the crystal was dried under reduced pressure under the condition of 40° C. to obtain tert-butyl [(1R,5S,6S)-6-aminomethyl-3-ethylbicyclo[3.2.0]hept-3-en-6-yl]acetate D-mandelate as a white powder (251.2 g, yield: 29.4%, 97.6% ee, 99.6% de).

$^1$H-NMR (400 MHz, DMSO-d6) δ ppm: 1.04 (3H, t, J=7.6 Hz), 1.28-1.35 (1H, m), 1.39 (9H, s), 1.96-2.11 (4H, m), 2.28 (1H, d, J=15.6 Hz), 2.33 (1H, d, J=15.6 Hz), 2.36-2.40 (1H, m), 2.72 (1H, quint, J=7.6 Hz), 3.00 (1H, d, J=13.2 Hz), 3.03 (1H, d, J=13.2 Hz), 3.31 (1H, br s), 4.54 (1H, s), 5.21-5.23 (1H, m), 7.13-7.25 (3H, m), 7.35-7.37 (2H, m).

$[α]_{20}^D$ -104.4° (C=0.108, MeOH).

Anal. calcd for $C_{24}H_{35}NO_5$: C, 69.04; H, 8.45; N, 3.35. Found C, 69.15; H, 8.46; N, 3.46.

Example 2

Tert-butyl [(1R,5S,6S)-6-(aminomethyl)bicyclo[3.2.0]hept-3-en-6-yl]acetate (S)—O-acetyl-mandelate

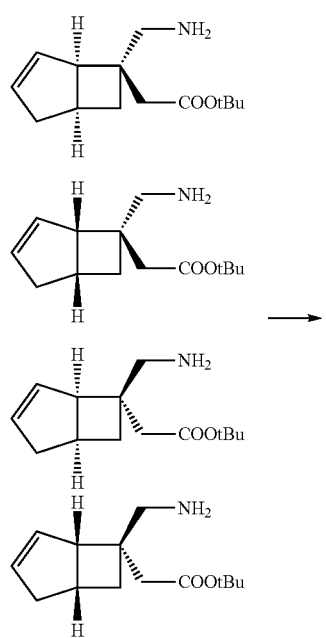

Acetonitrile (10 mL, 5.0 v/w) was added to tert-butyl [6-(aminomethyl)bicyclo[3.2.0]hept-3-en-6-yl]acetate (1.9 g, 8.0 mmol, 90:10 diastereomeric mixture). To the mixture, (S)—O-acetyl-mandelic acid (0.45 eq.) was added, and the mixture was stirred at room temperature. After 2.5 hours, the deposited crystal was filtered and washed with acetonitrile. The obtained crystal was dried under reduced pressure to obtain tert-butyl [(1R,5S,6S)-6-aminomethyl-3-ethylbicyclo[3.2.0]hept-3-en-6-yl]acetate (S)-β-acetyl-mandelate as a white crystal (0.904 g, yield: 26.2%, 90.4% ee, 99% de). This white crystal (620 mg) was suspended in acetonitrile (6.2 mL, 10.0 v/w), and the suspension was stirred at room temperature for 10 minutes. The resulting crystal was filtered, and the obtained crystal was dried under reduced pressure to obtain (S)—O-acetyl-mandelate as a white powder (557.6 mg, optical purity: 95.7% ee).

$^1$H-NMR (400 MHz, CD$_3$OD) δ ppm: 1.44-1.51 (1H, m), 1.45 (9H, s), 2.08-2.22 (2H, m), 2.13 (3H, s), 2.42 (2H, s), 2.50-2.57 (1H, m), 2.86 (1H, quint, J=7.6 Hz), 3.06-3.16 (1H, m), 3.25-3.33 (2H, m), 5.65-5.70 (1H, m), 5.74 (1H, s), 5.95-5.99 (1H, m), 7.25-7.34 (3H, m), 7.47-7.51 (2H, m).

$[α]_{20}^D$ -18.9° (C. 0.095, MeOH).

IR (KBr): cm$^{-1}$: 3046, 2977, 1726, 1584, 1235, 1144, 1028, 752.

MS (FAB$^+$): m/z: 238 (free+H)$^+$, MS (FAB+NaI): m/z: 260 (free+Na)$^+$, 217 (O-acetyl-mandelic acid+Na)$^+$.

Anal. calcd for $C_{24}H_{33}NO_6$: C, 66.80; H, 7.71; N, 3.25. Found C, 66.60; H, 7.72; N, 3.36.

Example 3

Tert-butyl [(1R,5S,6S)-6-aminomethyl-3-methylbicyclo[3.2.0]hept-3-en-6-yl]acetate D-mandelate A solvent (2.5 mL, 10 v/w) was added to tert-butyl [6-aminomethyl-3-methylbicyclo[3.2.0]hept-3-en-6-yl]acetate (237 mg, 1 mmol, 90:10 diastereomeric mixture). To the mixture, D-mandelic acid (0.5 eq.) was added, and the mixture was stirred for 2 hours under ice cooling. The deposited crystal was filtered. The obtained crystal was dried under reduced pressure to obtain D-mandelate at the yield and optical purity shown in Table 2 below. The optical purity was analyzed by converting the obtained salt into the free form with an aqueous sodium bicarbonate solution and then derivatizing the free form into a 3,5-dinitrobenzoyl form.

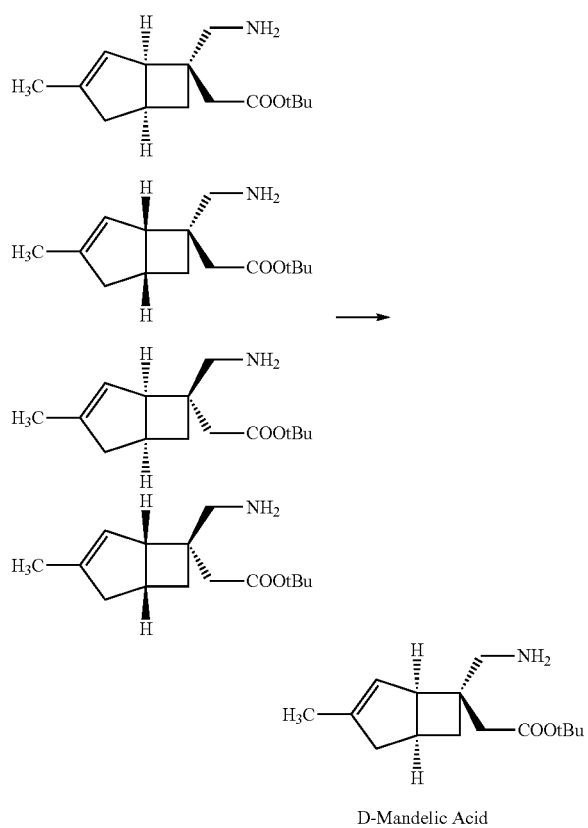

D-Mandelic Acid

TABLE 2

|   | Solvent | Yield | ee %[a] |
|---|---------|-------|---------|
| 1 | Acetonitrile | 8.5% | 48.5% ee |
| 2 | Ethyl acetate | 4.6% | 79.9% ee |
| 3 | Toluene | 11.2% | 85.0% ee |
| 4 | Cyclopentyl methyl ether | 13.8 | 82.4% ee |

3,5-Dinitrobenzoyl chloride, HPLC

HPLC analysis conditions (optical purity measurement, analyzed after derivatization into 3,5-dinitrobenzoyl form)

Column: CHIRALPAK AS-RH×2 (Daisel, 4.6 mm×150 mm, 5 μm)

Detection: 220 nm, Column temperature: 40° C., Flow rate: 0.8 ml/min

Mobile phase: MeCN/5 mM phosphate buffer (pH 7.0) =55/45

Retention time: 28.0 min, 23.6 min, 26.0 min $^1$H-NMR (400 MHz, CD$_3$OD): δ ppm: 1.45-1.51 (1H, m), 1.45 (9H, s), 1.82 (3H, s), 2.02-2.14 (2H, m), 2.41 (2H), 2.42-2.55 (1H, m), 2.85 (1H, quint, J=7.2 Hz), 3.06-3.13 (1H, m), 3.23 (1H, d, J=13.2 Hz), 3.26 (1H, d, J=13.2 Hz), 4.84 (1H, s), 5.25-5.28 (1H, m), 7.19-7.30 (3H, m), 7.44-7.47 (2H, m).

$[α]_{20}^D$ −97.4° (C. 0.102, MeOH).

IR (KBr): cm$^{-1}$: 3424, 2974, 2929, 1722, 1571, 1366, 1152, 1060, 755, 701.

MS (FAB$^+$): m/z: 252 (free+H)$^+$, MS (FAB+NaI): m/z: 274 (free+Na)$^+$, 175 (mandelic acid+Na)$^+$.

Steps of Deprotecting Ester Group and Forming Salt

Example 4

[(1R,5S,6S)-6-Aminomethyl-3-ethylbicyclo[3.2.0]hept-3-en-6-yl]acetic acid p-toluenesulfonate Tert-butyl [(1R,5S,6S)-6-aminomethyl-3-ethylbicyclo[3.2.0]hept-3-en-6-yl]acetate D-mandelate (4.17 g, 10 mmol) was suspended in toluene (21 ml). To the suspension, triethylamine (2.09 ml), and then water (21 ml) were added, and the mixture was stirred at room temperature. After 20 minutes, the organic layer was separated and extracted. The organic layer was washed again with water (10 ml) and then concentrated under reduced pressure to obtain the free form of tert-butyl [(1R,5S,6S)-6-aminomethyl-3-ethylbicyclo[3.2.0]hept-3-en-6-yl]acetate as an oil substance. Toluene (16 ml), and then p-toluenesulfonic acid monohydrate (2.28 g) were added thereto, and the mixture was stirred at 70° C. During the stirring, toluene (15 ml) was further added, and after 3 hours, the mixture was allowed to cool. The deposited solid was filtered, then washed with toluene, and then dried under reduced pressure to obtain [(1R,5S,6S)-6-aminomethyl-3-ethylbicyclo[3.2.0]hept-3-en-6-yl]acetic acid p-toluenesulfonate as a white powder (3.90 g).

$^1$H-NMR (400 MHz, CD$_3$OD) δ ppm: 1.10 (3H, t, J=7.2 Hz), 1.49 (1H, dd, J=7.4, 12.4 Hz), 2.06-2.20 (4H, m), 2.37 (3H, s), 2.49-2.55 (1H, m), 2.51 (2H, s), 2.87 (1H, quint, J=7.4 Hz), 3.12 (1H, br S), 3.29 (1H, d, J=13.3 Hz), 3.33 (1H, d, J=13.3 Hz), 5.31-5.32 (1H, m), 7.22-7.25 (2H, m), 7.69-7.72 (2H, m).

$[α]_{20}^D$ −56.1° (C. 0.108, MeOH).

IR (KBr): cm$^{-1}$: 3149, 2962, 1708, 1498, 1237, 1164, 1038, 1011, 813, 680, 566.

MS (FAB$^+$): m/z: 210 (free+H)$^+$, 412 (2Mfree+H)$^+$.

Example 5

[(1R,5S,6S)-6-(Aminomethyl)bicyclo[3.2.0]hept-3-en-6-yl]acetic acid benzenesulfonate Tert-butyl [(1R,5S,6S)-6-(aminomethyl)bicyclo[3.2.0]hept-3-en-6-yl]acetate (S)-β-acetyl-mandelate (116 mg, 0.269 mmol) was suspended in anisole (0.58 ml). To the suspension, water (0.6 ml), and then triethylamine (0.045 ml) were added, and the mixture was stirred at room temperature. After 15 minutes, the organic layer was separated and extracted. The organic layer was washed again with water (300 ml) and then concentrated under reduced pressure to obtain a solution of the free form of tert-butyl [(1R,5S,6S)-6-(aminomethyl)bicyclo[3.2.0]hept-3-en-6-yl]acetate in anisole. Benzenesulfonic acid (46 mg) was added thereto, and the mixture was stirred at 70° C. for 1.25 hours and allowed to cool. The deposited solid was filtered, and the filtered powder was washed again by pouring acetone, and dried under reduced pressure to obtain [(1R,5S,6S)-6-(aminomethyl)bicyclo[3.2.0]hept-3-en-6-yl]acetic acid benzenesulfonate as a white powder (55.5 mg).

$^1$H-NMR (400 MHz, CD$_3$OD) δ ppm: 1.51 (1H, dd, J=7.6, 12.4 Hz), 2.12-2.20 (2H, m), 2.51 (2H, s), 2.51-2.57 (1H, m), 2.88 (1H, quint, J=7.4 Hz), 3.17-3.18 (1H, m), 3.32 (1H, d, J=13.3 Hz), 3.36 (1H, d, J=13.3 Hz), 5.69-5.71 (1H, m), 5.97-5.99 (1H, m), 7.39-7.44 (3H, m), 7.81-7.84 (2H, m).

$[α]_{20}^D$ −99.7° (C 0.09, MeOH).

IR (KBr): cm$^{-1}$: 3125, 3054, 2988, 1705, 1515, 1412, 1237, 1163, 1121, 1016, 730, 689, 621, 563.

MS (FAB$^+$): m/z: 182 (free+H)$^+$, m/z: 363 (2Mfree+H)$^+$.

Anal. calcd for $C_{16}H_{21}NO_5S$: C, 56.62; H, 6.24; N, 4.13. Found C, 56.19; H, 6.21; N, 4.13.

FREE TEXT FOR SEQUENCE LISTING

SEQ ID NO: 1: PCR sense primer for the first half fragment of human Cacna2d1.
SEQ ID NO: 2: PCR antisense primer for the first half fragment of human Cacna2d1.
SEQ ID NO: 3: PCR sense primer for the second half fragment of human Cacna2d1.
SEQ ID NO: 4: PCR antisense primer for the second half fragment of human Cacna2d1.
SEQ ID NO: 5: multicloning site of a vector pBluescript 2.

The invention claimed is:

1. A method for producing a compound represented by formula (I) or a salt thereof by optical resolution:

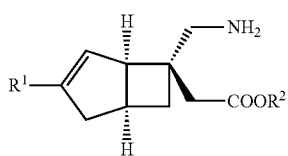

the method comprising:

dissolving a mixture of compounds represented by formulas (II), (III), (IV), and (V) and an optically active organic acid in a solvent:

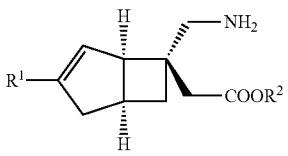

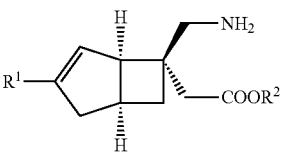

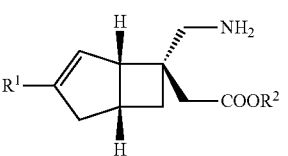

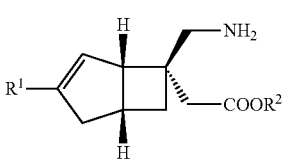

and then depositing a crystal, wherein:
R$^1$ is a hydrogen atom or a C$_1$-C$_6$ alkyl group, and
R$^2$ is a hydrogen atom or a protective group for the carboxy group.

2. The method for producing a compound represented by formula (I) or a salt thereof according to claim 1, wherein R$^1$ is a hydrogen atom, a methyl group, or an ethyl group.

3. The method for producing a compound represented by formula (I) or a salt thereof according to claim 1, wherein R$^2$ is a t-butyl group.

4. The method for producing a compound represented by formula (I) or a salt thereof according to claim 1, wherein the optically active organic acid is at least one active organic acid selected from the following group: D-mandelic acid, L-mandelic acid, Di-p-toluoyl-L-tartaric acid, N-Boc-L-proline, (R)-α-methoxyphenylacetic acid, O-acetyl-L-mandelic acid, Di-benzoyl-L-tartaric acid, O-acetyl-D-mandelic acid, N-Boc-L-alanine, (S)-2-(6-methoxy-2-naphthyl)propionic acid, diacetyl-L-tartaric acid, L-tartaric acid, L-malic acid, L-pyroglutamic acid, (+)-camphoric acid, (S)-2-methylglutamic acid, (+)-3-bromocamphor-8-sulfonic acid, (−)-menthoxyacetic acid, and (S)-2-phenoxypropionic acid.

5. The method for producing a compound represented by formula (I) or a salt thereof according to claim 1, wherein the solvent is at least one solvent selected from the following group:

acetonitrile, ethyl acetate, toluene, and cyclopentyl methyl ether.

6. A method for producing a compound represented by formula (X) or a salt thereof:

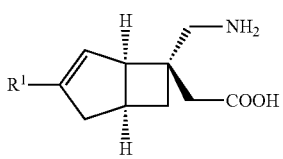

wherein:
R$^1$ is a hydrogen atom or a C$_1$-C$_6$ alkyl group,
the method comprising:
producing a compound represented by formula (I) by a production method according to claim 1;
removing R$^2$ from the compound represented by formula (I); and optionally forming an acid or a salt of the compound of formula (I).

* * * * *

SEQUENCE LISTING

```
<160> NUMBER OF SEQ ID NOS: 7

<210> SEQ ID NO 1
<211> LENGTH: 42
<212> TYPE: DNA
<213> ORGANISM: Artificial
<220> FEATURE:
<223> OTHER INFORMATION: PCR sense primer for human Cacna2d1 front

<400> SEQUENCE: 1
agctgcggcc gctagcgcca ccatggctgg ctgcctgctg gc            42

<210> SEQ ID NO 2
<211> LENGTH: 27
<212> TYPE: DNA
<213> ORGANISM: Artificial
<220> FEATURE:
<223> OTHER INFORMATION: PCR antisense primer for human Cacna2d1 front

<400> SEQUENCE: 2
attaggatcg attgcaaagt aataccc                              27

<210> SEQ ID NO 3
<211> LENGTH: 26
<212> TYPE: DNA
<213> ORGANISM: Artificial
<220> FEATURE:
<223> OTHER INFORMATION: PCR sense primer for human Cacna2d1 rear

<400> SEQUENCE: 3
aatgggtatt actttgcaat cgatcc                               26

<210> SEQ ID NO 4
<211> LENGTH: 32
<212> TYPE: DNA
<213> ORGANISM: Artificial
<220> FEATURE:
<223> OTHER INFORMATION: PCR antisense primer for human Cacna2d1 rear

<400> SEQUENCE: 4
agtcggatcc tcataacagc cggtgtgtgc tg                        32

<210> SEQ ID NO 5
<211> LENGTH: 98
<212> TYPE: DNA
<213> ORGANISM: Artificial
<220> FEATURE:
<223> OTHER INFORMATION: multi cloning site of vector pBluescript 2

<400> SEQUENCE: 5
ccaccgcggt ggcggccgct ctagaactag tggatccccc gggctgcagg aattcgatat   60
caagcttatc gataccgtcg acctcgaggg ggggcccg                         98

<210> SEQ ID NO 6
<211> LENGTH: 1573
<212> TYPE: DNA
```

<213> ORGANISM: Homo sapiens

<400> SEQUENCE: 6

| | | |
|---|---|---|
| ggcggccgct agcgccacca tggctgctgg ctgcctgctg gccttgactc tgacactttt | 60 |
| ccaatctttg ctcatcggcc cctcgtcgga ggagccgttc ccttcggccg tcactatcaa | 120 |
| atcatgggtg ataagatgc aagaagacct tgtcacactg gcaaaaacag caagtggagt | 180 |
| caatcagctt gttgatattt atgagaaata tcaagatttg tatactgtgg aaccaaataa | 240 |
| tgcacgccag ctggtagaaa ttgcagccag ggatattgag aaacttctga gcaacagatc | 300 |
| taaagccctg gtgcgcctgg cattggaagc ggagaaagtt caagcagctc accagtggag | 360 |
| agaagatttt gcaagcaatg aagttgtcta ctacaatgca aggatgatc tcgatcctga | 420 |
| gaaaaatgac agtgagccag gcagccagag gataaaacct gttttcattg aagatgctaa | 480 |
| ttttggacga caaatatctt atcagcacgc agcagtccat attcctactg acatctatga | 540 |
| gggctcaaca attgtgttaa atgaactcaa ctggacaagt gccttagatg aagttttcaa | 600 |
| aaagaatcgc gaggaagacc cttcattatt gtggcaggtt tttggcagtg ccactggcct | 660 |
| agctcgatat tatccagctt caccatgggt tgataatagt agaactccaa ataagattga | 720 |
| ccttttatgat gtacgcagaa gaccatggta catccaagga gctgcatctc ctaaagacat | 780 |
| gcttattctg gtggatgtga gtggaagtgt tagtggattg acacttaaac tgatccgaac | 840 |
| atctgtctcc gaaatgttag aaaccctctc agatgatgat ttcgtgaatg tagcttcatt | 900 |
| taacagcaat gctcaggatg taagctgttt tcagcacctt gtccaagcaa atgtaagaaa | 960 |
| taaaaaagtg ttgaaagacg cggtgaataa tatcacagcc aaaggaatta cagattataa | 1020 |
| gaagggcttt agttttgctt ttgaacagct gcttaattat aatgtttcca gagcaaactg | 1080 |
| caataagatt attatgctat tcacggatgg aggagaagag agagcccagg agatatttaa | 1140 |
| caaatacaat aaagataaaa agtacgtgt attcacgttt tcagttggtc aacacaatta | 1200 |
| tgacagagga cctattcagt ggatggcctg tgaaaacaaa ggttattatt atgaaattcc | 1260 |
| ttccattggt gcaataagaa tcaatactca ggaatatttg gatgttttgg gaagaccaat | 1320 |
| ggttttagca ggagacaaag ctaagcaagt ccaatggaca aatgtgtacc tggatgcatt | 1380 |
| ggaactggga cttgtcatta ctggaactct tccggtcttc aacataaccg gccaatttga | 1440 |
| aaataagaca aacttaaaga accagctgat tcttggtgtg atgggagtag atgtgtcttt | 1500 |
| ggaagatatt aaaagactga caccacgttt tacactgtgc cccaatgggt attactttgc | 1560 |
| aatcgatcct aat | 1573 |

<210> SEQ ID NO 7
<211> LENGTH: 3301
<212> TYPE: DNA
<213> ORGANISM: Homo sapiens

<400> SEQUENCE: 7

| | | |
|---|---|---|
| ggcggccgct agcgccacca tggctgctgg ctgcctgctg gccttgactc tgacactttt | 60 |
| ccaatctttg ctcatcggcc cctcgtcgga ggagccgttc ccttcggccg tcactatcaa | 120 |
| atcatgggtg ataagatgc aagaagacct tgtcacactg gcaaaaacag caagtggagt | 180 |
| caatcagctt gttgatattt atgagaaata tcaagatttg tatactgtgg aaccaaataa | 240 |
| tgcacgccag ctggtagaaa ttgcagccag ggatattgag aaacttctga gcaacagatc | 300 |
| taaagccctg gtgcgcctgg cattggaagc ggagaaagtt caagcagctc accagtggag | 360 |
| agaagatttt gcaagcaatg aagttgtcta ctacaatgca aggatgatc tcgatcctga | 420 |

```
gaaaaatgac agtgagccag gcagccagag gataaaacct gttttcattg aagatgctaa    480
ttttggacga caaatatctt atcagcacgc agcagtccat attcctactg acatctatga    540
gggctcaaca attgtgttaa atgaactcaa ctggacaagt gccttagatg aagttttcaa    600
aaagaatcgc gaggaagacc cttcattatt gtggcaggtt tttggcagtg ccactggcct    660
agctcgatat tatccagctt caccatgggt tgataatagt agaactccaa ataagattga    720
cctttatgat gtacgcagaa gaccatggta catccaagga gctgcatctc ctaaagacat    780
gcttattctg gtggatgtga gtggaagtgt tagtggattg acacttaaac tgatccgaac    840
atctgtctcc gaaatgttag aaaccctctc agatgatgat ttcgtgaatg tagcttcatt    900
taacagcaat gctcaggatg taagctgttt tcagcacctt gtccaagcaa atgtaagaaa    960
taaaaaagtg ttgaaagacg cggtgaataa tatcacagcc aaaggaatta cagattataa    1020
gaagggcttt agttttgctt ttgaacagct gcttaattat aatgtttcca gagcaaactg    1080
caataagatt attatgctat tcacggatgg aggagaagag agagcccagg agatatttaa    1140
caaatacaat aaagataaaa agtacgtgt attcacgttt tcagttggtc aacacaatta    1200
tgacagagga cctattcagt ggatggcctg tgaaaacaaa ggttattatt atgaaattcc    1260
ttccattggt gcaataagaa tcaatactca ggaatatttg gatgttttgg aagaccaat     1320
ggttttagca ggagacaaag ctaagcaagt ccaatggaca aatgtgtacc tggatgcatt    1380
ggaactggga cttgtcatta ctggaactct tccggtcttc aacataaccg gccaatttga    1440
aaataagaca aacttaaaga accagctgat tcttggtgtg atgggagtag atgtgtcttt    1500
ggaagatatt aaaagactga caccacgttt tacactgtgc cccaatgggt attactttgc    1560
aatcgatcct aatggttatg ttttattaca tccaaatctt cagccaaaga accccaaatc    1620
tcaggagcca gtaacattgg atttccttga tgcagagtta gagaatgata ttaaagtgga    1680
gattcgaaat aagatgattg atggggaaag tggagaaaaa acattcagaa ctctggttaa    1740
atctcaagat gagagatata ttgacaaagg aaacaggaca tacacatgga cacctgtcaa    1800
tggcacagat tacagtttgg ccttggtatt accaacctac agttttact atataaaagc    1860
caaactagaa gagacaataa ctcaggccag atcaaaaaag gcaaaatga aggattcgga    1920
aaccctgaag ccagataatt ttgaagaatc tggctataca ttcatagcac caagagatta    1980
ctgcaatgac ctgaaaatat cggataataa cactgaattt cttttaaatt tcaacgagtt    2040
tattgataga aaaactccaa acaacccatc atgtaacgcg gatttgatta atagagtctt    2100
gcttgatgca ggctttacaa atgaacttgt ccaaaattac tggagtaagc agaaaaatat    2160
caagggagtg aaagcacgat tgttgtgac tgatggtggg attaccagag tttatcccaa    2220
agaggctgga gaaaattggc aagaaaaccc agagacatat gaggacagct tctataaaag    2280
gagcctagat aatgataact atgttttcac tgctccctac tttaacaaaa gtggacctgg    2340
tgcctatgaa tcgggcatta tggtaagcaa agctgtagaa atatatattc aagggaaact    2400
tcttaaacct gcagttgttg aattaaaat tgatgtaaat tcctggatag agaatttcac    2460
caaaaccctca atcagagatc cgtgtgctgg tccagtttgt gactgcaaaa gaaacagtga    2520
cgtaatggat tgtgtgattc tggatgatgg tgggtttctt ctgatggcaa atcatgatga    2580
ttatactaat cagattggaa gattttttgg agagattgat cccagcttga tgagacacct    2640
ggttaatata tcagtttatg cttttaacaa atcttatgat tatcagtcag tatgtgagcc    2700
cggtgctgca ccaaaacaag gagcaggaca tcgctcagca tatgtgccat cagtagcaga    2760
catattacaa attggctggt gggccactgc tgctgcctgg tctattctac agcagtttct    2820
```

-continued

```
cttgagtttg accttttccac gactccttga ggcagttgag atggaggatg atgacttcac  2880
ggcctccctg tccaagcaga gctgcattac tgaacaaacc cagtatttct tcgataacga  2940
cagtaaatca ttcagtggtg tattagactg tggaaactgt tccagaatct ttcatggaga  3000
aaagcttatg aacaccaact taatattcat aatggttgag agcaaaggga catgtccatg  3060
tgacacacga ctgctcatac aagcggagca gacttctgac ggtccaaatc cttgtgacat  3120
ggttaagcaa cccagatacc gaaaagggcc tgatgtctgc tttgataaca atgtcttgga  3180
ggattatact gactgtggtg gtgtttctgg attaaatccc tccctgtggt atatcattgg  3240
aatccagttt ctactacttt ggctggtatc tggcagcaca caccggctgt tatgaggatc  3300
c                                                                  3301
```